United States Patent
Chang et al.

(10) Patent No.: US 10,309,875 B2
(45) Date of Patent: Jun. 4, 2019

(54) SAMPLE COLLECTION COMPONENT AND MANUFACTURING METHOD THEREOF

(71) Applicant: Materials Analysis Technology Inc., Hsinchu County (TW)

(72) Inventors: Pin Chang, Hsinchu (TW); Ying-Chan Hung, Changhua County (TW); Hung-Jen Chen, Hsinchu (TW)

(73) Assignee: Materials Analysis Technology Inc., Hsinchu County (TW)

( * ) Notice: Subject to any disclaimer, the term of this patent is extended or adjusted under 35 U.S.C. 154(b) by 418 days.

(21) Appl. No.: 15/063,514

(22) Filed: Mar. 8, 2016

(65) Prior Publication Data

US 2017/0176298 A1    Jun. 22, 2017

(30) Foreign Application Priority Data

Dec. 22, 2015  (TW) .............................. 104143103 A

(51) Int. Cl.
| | |
|---|---|
| *G01N 1/02* | (2006.01) |
| *G01N 23/2204* | (2018.01) |
| *H01J 37/00* | (2006.01) |
| *G02B 21/00* | (2006.01) |
| *G02B 5/20* | (2006.01) |

(52) U.S. Cl.
CPC ........... *G01N 1/02* (2013.01); *G01N 23/2204* (2013.01); *G02B 5/208* (2013.01); *G02B 21/00* (2013.01); *H01J 37/00* (2013.01)

(58) Field of Classification Search
CPC ....... G01N 1/02; G01N 23/2204; H01J 37/00; G02B 5/208; G02B 21/00
See application file for complete search history.

(56) References Cited

U.S. PATENT DOCUMENTS

| | | | |
|---|---|---|---|
| 6,037,168 A | 3/2000 | Brown | |
| 6,410,925 B1 | 6/2002 | Armbruster et al. | |
| 7,807,979 B2 * | 10/2010 | Liu | H01J 37/20 250/306 |
| 8,829,469 B2 | 9/2014 | Damiano, Jr. et al. | |
| 2008/0135778 A1 | 6/2008 | Liu et al. | |

(Continued)

FOREIGN PATENT DOCUMENTS

| | | |
|---|---|---|
| JP | H09173049 | 7/1997 |
| JP | 2004069346 | 3/2004 |

(Continued)

OTHER PUBLICATIONS

"Office Action of Taiwan Counterpart Application", dated Jul. 11, 2016, p. 1-p. 8.

(Continued)

*Primary Examiner* — Daniel S Larkin
*Assistant Examiner* — Anthony W Megna Fuentes
(74) *Attorney, Agent, or Firm* — JCIPRNET

(57) ABSTRACT

A sample collection component including a main body and a removable light shielding component is provided. The main body has a sample storing space which is sealable and allows light to pass through. The removable light shielding component is disposed on the main body and located outside the sample storing space for shielding at least a portion of the light passing through the sample storing space. In addition, a manufacturing method of the sample collection component is also provided.

9 Claims, 10 Drawing Sheets

(56) References Cited

U.S. PATENT DOCUMENTS

| | | |
|---|---|---|
| 2012/0120226 A1 | 5/2012 | de Jonge |
| 2012/0298883 A1 | 11/2012 | Grogan et al. |
| 2013/0009072 A1* | 1/2013 | Chen ................. H01J 37/20 |
| | | 250/440.11 |
| 2016/0042912 A1* | 2/2016 | Adiga ................. H01J 37/20 |
| | | 250/440.11 |

FOREIGN PATENT DOCUMENTS

| | | |
|---|---|---|
| JP | 2007170984 | 7/2007 |
| TW | 201409011 | 3/2014 |

OTHER PUBLICATIONS

"Office Action of Japan Counterpart Application," dated Jul. 18, 2017, p. 1-p. 7.

* cited by examiner

SAMPLE COLLECTION COMPONENT AND MANUFACTURING METHOD THEREOF

CROSS-REFERENCE TO RELATED APPLICATION

This application claims the priority benefit of Taiwan application serial no. 104143103, filed on Dec. 22, 2015. The entirety of the above-mentioned patent application is hereby incorporated by reference herein and made a part of this specification.

BACKGROUND OF THE INVENTION

Field of the Invention

The invention relates to a sample collection component and a manufacturing method thereof, and more particularly relates to a sample collection component having a light shielding component and a manufacturing method thereof.

Description of Related Art

With the advance in microscopy technology, various devices for microscopic observation, such as atomic force microscope (AFM), electron microscope (e.g., transmission electron microscope (TEM) and scanning electron microscope (SEM)), and so on, have been invented. Different types of sample collection components are required for different microscopes.

In terms of the current sample collection components, however, before and after a liquid sample is loaded into the sample storing space of the sample collection component, irradiation of external light may provide energy to the liquid sample or cause the temperature of the liquid sample to change. As a result, fluidity of the liquid sample may change, the components of the liquid sample may react with each other, or the sample composition may even deteriorate, and affect the final observation result of the display device.

SUMMARY OF THE INVENTION

The invention provides a sample collection component, which efficiently shields light before and after a liquid sample is loaded into the sample collection component.

The invention provides a manufacturing method of a sample collection component, by which a removable light shielding component is further disposed on a main body of the sample collection component to shield at least a portion of the light that passes through a storing space of the sample collection component.

The invention provides a manufacturing method for manufacturing a sample collection component that includes a removable light shielding component for shielding at least a portion of the light that passes through a storing space of the sample collection component.

A sample collection component of the invention includes a main body and a removable light shielding component. The main body has a sample storing space that is sealable and allows light to pass through. The removable light shielding component is disposed on the main body and located outside the sample storing space for shielding at least a portion of the light that passes through the sample storing space.

A manufacturing method of a sample collection component of the invention includes bonding a first substrate to a second substrate, and forming a spacer between the first substrate and the second substrate to connect and fix the first substrate and the second substrate, so as to form a sample storing space, which is sealable and allows light to pass through, between the first substrate and the second substrate. A removable light shielding component is formed on the first substrate. The removable light shielding component corresponds to the sample storing space for shielding at least a portion of the light that passes through the sample storing space.

A manufacturing method of a sample collection component of the invention includes providing a first substrate. A removable light shielding component is formed on the first substrate in the process of manufacturing the first substrate. The first substrate is bonded to a second substrate. A spacer is formed between the first substrate and the second substrate to connect and fix the first substrate and the second substrate, so as to form a sample storing space that is sealable and allows light to pass through between the first substrate and the second substrate. The removable light shielding component corresponds to the sample storing space for shielding at least a portion of the light that passes through the sample storing space.

According to an embodiment of the invention, the removable light shielding component includes a sheet material. The sheet material is attached onto the main body and covers at least a portion of the sample storing space.

According to an embodiment of the invention, the main body includes a recess corresponding to the sample storing space, for forming an observation window that exposes the sample storing space. The sheet material seals the recess to form a sealed space of a particular pressure in the recess.

According to an embodiment of the invention, the removable light shielding component includes a material layer. The material layer covers a surface of the main body and at least a portion of the sample storing space.

According to an embodiment of the invention, the removable light shielding component includes a structural member that is manufactured simultaneously with the main body. The structural member is connected with the main body by a connection part.

According to an embodiment of the invention, the main body includes a recess corresponding to the sample storing space for forming an observation window that exposes the sample storing space. The removable light shielding component includes a material layer that is located on a bottom surface of the observation window and extends to a portion of a junction between the sample storing space and the main body.

According to an embodiment of the invention, the main body includes a first substrate, a second substrate, and a spacer. The first substrate has a first surface and a second surface opposite to each other. The second substrate has a third surface and a fourth surface opposite to each other. The first substrate and the second substrate are stacked on each other and the second surface faces the third surface. The spacer is disposed between the second surface and the third surface and connects and fixes the first substrate and the second substrate to form the sample storing space between the first substrate and the second substrate.

According to an embodiment of the invention, the main body further includes a first thin film and a second thin film. The first thin film is located on the second surface of the first substrate. The second thin film is located on the third surface of the second substrate. The first thin film, the second thin film, and the spacer together surround the sample storing space.

According to an embodiment of the invention, the first substrate includes a first recess located on the first surface and a bottom of the first recess is connected with the first thin film to form an observation window that exposes the sample storing space. The removable light shielding component includes a material layer. The material layer is located on a bottom surface of the observation window and extends to a portion of a junction between the sample storing space and the main body.

According to an embodiment of the invention, the second substrate includes a second recess located on the fourth surface. A bottom of the second recess is connected with the second thin film to form a second observation window that exposes the sample storing space.

According to an embodiment of the invention, the removable light shielding component includes a light filtering material or a light valve component.

According to an embodiment of the invention, a material of the removable light shielding component is a conductor of gold, copper, or aluminum, or a semiconductor of silicon or a non-conductor of plastic, ceramics, or a polymer material.

According to an embodiment of the invention, the light filtering material filters a light having a wavelength of 100 nm to 1 mm.

According to an embodiment of the invention, a method of forming the removable light shielding component includes attaching a sheet material onto the first substrate. The sheet material covers at least a portion of the sample storing space.

According to an embodiment of the invention, a material of the sheet material is a conductor of gold, copper, or aluminum, or a semiconductor of silicon, or a non-conductor of plastic, ceramics, or a polymer material.

According to an embodiment of the invention, the manufacturing method of the sample collection component further includes forming a recess on a first surface of the first substrate corresponding to the sample storing space for forming an observation window that exposes the sample storing space. The sheet material seals the recess to form a sealed space of a particular pressure in the recess.

According to an embodiment of the invention, a method of attaching the sheet material onto the first substrate includes attaching the sheet material onto the first substrate by bonding, clamping, or electrostatic adsorption from outside of the first substrate.

According to an embodiment of the invention, a method of forming the removable light shielding component includes forming a material layer on the first surface of the first substrate. The sheet material covers at least a portion of the sample storing space.

According to an embodiment of the invention, a method of forming the material layer on the first substrate includes applying the material layer onto the first substrate by vapor deposition, sputtering, or coating.

According to an embodiment of the invention, the removable light shielding component includes a structural member that is manufactured simultaneously with the first substrate, and the structural member is connected with the first substrate by a connection part.

According to an embodiment of the invention, the manufacturing method of the sample collection component further includes forming a recess on a first surface of the first substrate corresponding to the sample storing space for forming an observation window that exposes the sample storing space. The removable light shielding component includes a material layer. The material layer is located on a bottom surface of the observation window and extends to a portion of a junction between the sample storing space and the first substrate.

Based on the above, the sample collection component of the invention shields and filters at least a portion of the light, which enters the sample storing space through the main body, with the removable light shielding component. Therefore, before and after the liquid sample is loaded into the sample storing space of the sample collection component, the removable light shielding component shields the light and prevents the fluidity or component properties of the liquid sample from being changed due to reaction between the components of the liquid sample and the incident light, which may affect the subsequent observation result.

To make the aforementioned and other features and advantages of the invention more comprehensible, several embodiments accompanied with drawings are described in detail as follows.

BRIEF DESCRIPTION OF THE DRAWINGS

The accompanying drawings are included to provide a further understanding of the invention, and are incorporated in and constitute a part of this specification. The drawings illustrate exemplary embodiments of the invention and, together with the description, serve to explain the principles of the invention.

DESCRIPTION OF THE EMBODIMENTS

Figure 1A:
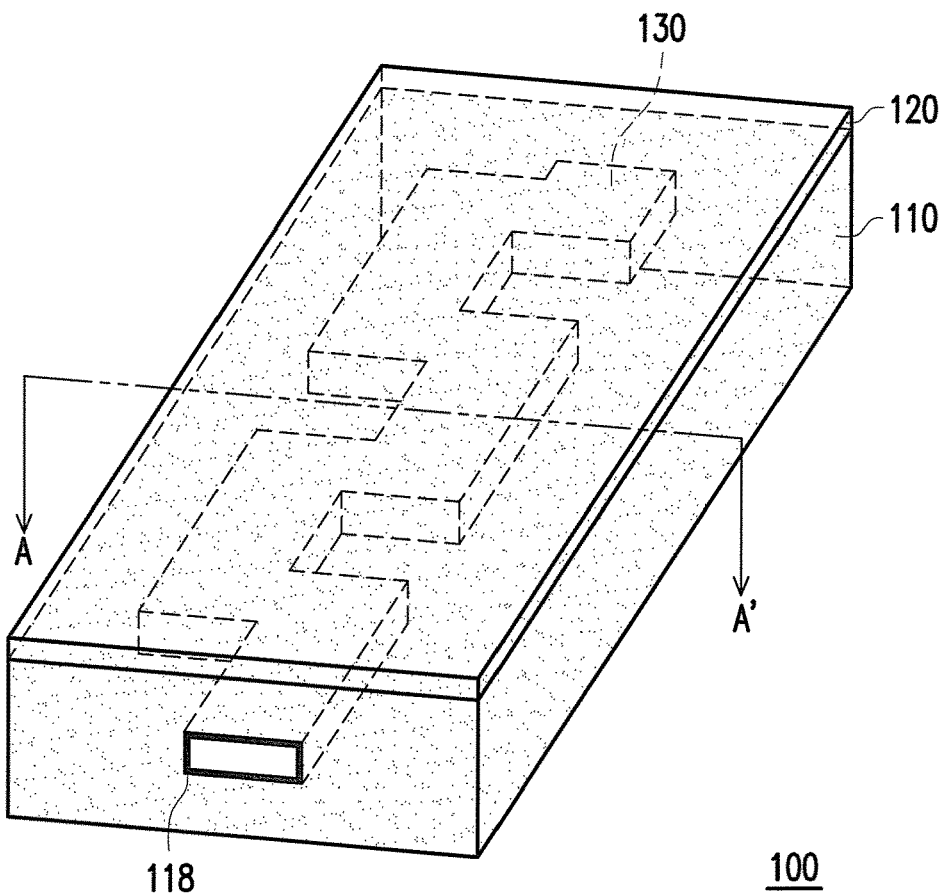
FIG. 1A is a schematic view of the sample collection component according to an embodiment of the invention.

FIG. 1A is a schematic view of a sample collection component according to an embodiment of the invention.

Figure 1B:
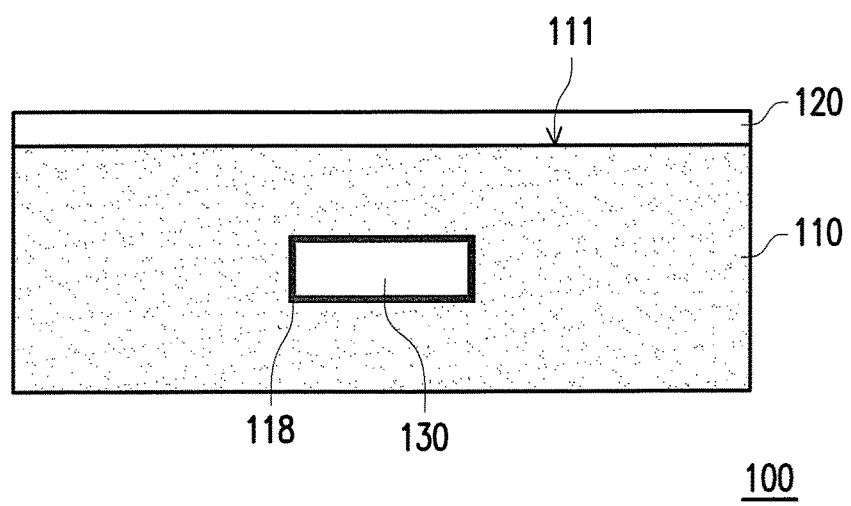
FIG. 1B is a schematic cross-sectional view of the sample collection component of FIG. 1A along the plane A-A'.

FIG. 1B is a schematic cross-sectional view of the sample collection component of FIG. 1A along the plane A-N. A sample collection component 100 includes a main body 110 and a removable light shielding component 120. In this embodiment, the main body 110 has a sample storing space 130 that is sealable. The sample storing space 130 allows light to pass through. Moreover, a removable light shielding component 120 is disposed on the main body 110 and located outside the sample storing space 130.

In this embodiment, the removable light shielding component 120 is a sheet material, for example, which is attached onto the main body 110 to cover a portion of the sample storing space 130. The sheet material may be formed of a conductive material, such as gold, copper, and aluminum. Alternatively, the sheet material may be formed of silicon, plastic, ceramics, a polymer conductor, or a semiconductor material. For example, the removable light shielding component 120 may be a copper foil, which may be attached to a surface 111 of the main body 110 by bonding, clamping, or electrostatic adsorption. Moreover, in this embodiment, the removable light shielding component 120 may be a material layer composed of a metal, such as gold and aluminum, which is formed by sputtering, vapor deposition, or spin coating and covers the surface 111 of the main body 110 and a portion of the sample storing space 130.

The removable light shielding component 120 may include a light filtering component formed of an organic material and a metal material, or a light valve component formed of a liquid crystal material, for example. The removable light shielding component 120 may shield a portion of the light that enters the main body 110 by filtering, absorbing, or reflecting the light. If the removable light shielding component 120 is formed of a light filtering material, the light shielded by the removable light shielding component 120 has a wavelength that ranges from 100 nm to 1 mm, i.e., a range between UVC and LWIR, for example.

In this embodiment, the main body 110 of the sample collection component 100 is provided with the removable light shielding component 120 thereon. Therefore, before and after a liquid sample to be observed is loaded into the sample storing space 130, the removable light shielding component 120 is temporarily fixed to cover the main body 110 to prevent a visible light, such as ultraviolet light, or an invisible light, such as infrared light, from passing through the main body 110 of the sample collection component 100 and irradiating the sample storing space 130 and causing components of the liquid sample to react or change in property due to the light irradiation. Moreover, after the loading of the liquid sample is completed, the removable light shielding component 120 may be removed to facilitate observation of the sample performed by using a microscope device, such as an electron microscope. In addition, in this embodiment, a thin film 118 may be further disposed in a periphery of the sample storing space 130 to serve as a surface of contact between the sample storing space 130 and the liquid sample, so as to enhance flow or adsorption of the liquid sample in the sample storing space 130.

In this embodiment, after the loading of the liquid sample into the sample storing space 130 is completed, the removable light shielding component 120 may be removed by a physical method, such as applying an external force, current, or electric field, and changing the temperature, or by a chemical method, such as dissolution, etching, or other chemical reactions, according to different composition structures, materials, and forming methods.

Figure 2:
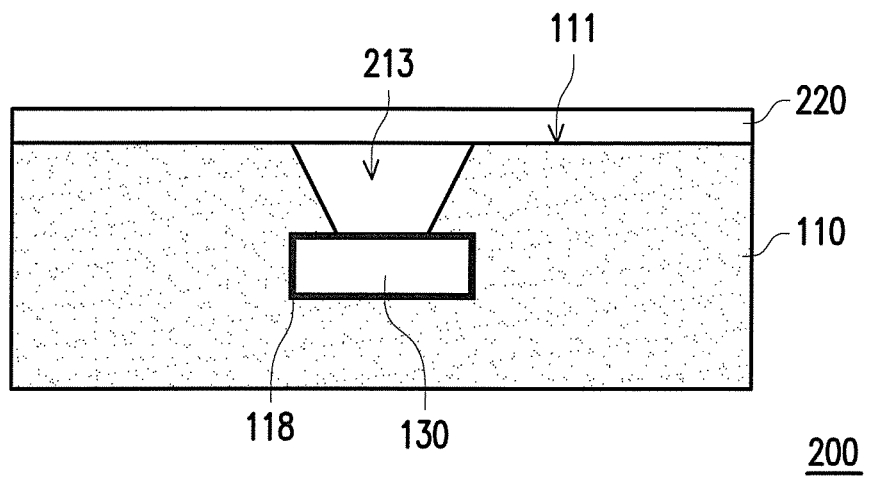
FIG. 2 is a schematic view of the sample collection component according to another embodiment of the invention.

FIG. 2 is a schematic view of the sample collection component according to another embodiment of the invention. A sample collection component 200 of this embodiment has a structure similar to the structure of the sample collection component 100 of the previous embodiment. Therefore, identical or similar components are assigned with the same or similar reference numerals, and detailed description thereof is not repeated hereinafter. In this embodiment, the main body 110 of the sample collection component 200 may further has a recess corresponding to the sample storing space 130 for forming an observation window 213 that exposes the sample storing space 130. Moreover, in this embodiment, the sample collection component 200 includes a removable light shielding component 220, which may be a sheet material. The sheet material is used to seal the recess where the observation window 213 is formed, so as to form a sealed space of a particular pressure in the recess. The pressure is in a range of about 0.01 KPa to 150 KPa. For example, the pressure of the sealed space may be smaller than or greater than an external pressure, such that the removable light shielding component 220 is more securely attached to the surface 111 of the main body 110 due to the difference between the internal and external pressures, so as to form an airtight space in the sealed space.

Figure 3:
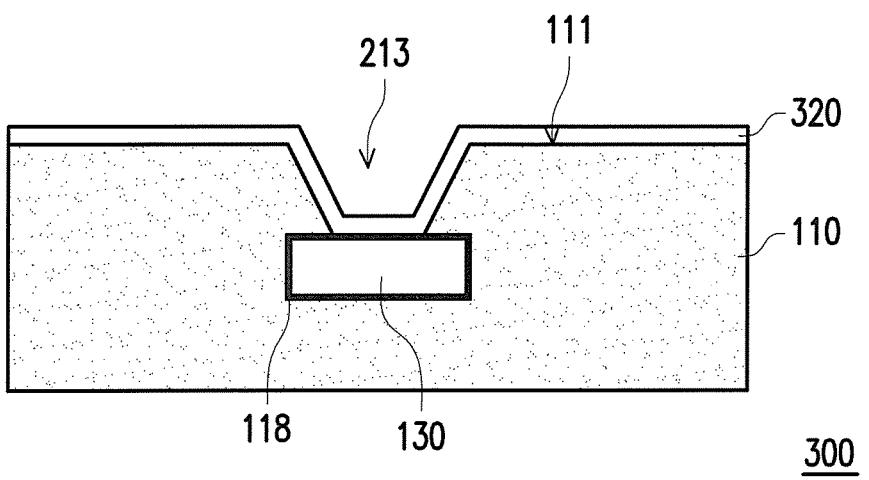
FIG. 3 is a schematic view of the sample collection component according to another embodiment of the invention.

FIG. 3 is a schematic view of the sample collection component according to another embodiment of the invention. A sample collection component 300 of this embodiment has a structure similar to the structure of the sample collection component 200 of the embodiment of FIG. 2. Therefore, identical or similar components are assigned with the same or similar reference numerals, and detailed description thereof is not repeated hereinafter. A difference between the sample collection component 300 of this embodiment and the sample collection component 200 of the previous embodiment is that: a removable light shielding component 320 of this embodiment is a metal material layer, such as gold and aluminum, forming by sputtering, vapor deposition, or spin coating, for example. As shown in FIG. 3, the removable light shielding component 320 may be disposed on a bottom surface of the observation window 213 and extend to a portion of a junction between the sample storing space 130 and the main body 110.

Figure 4A:
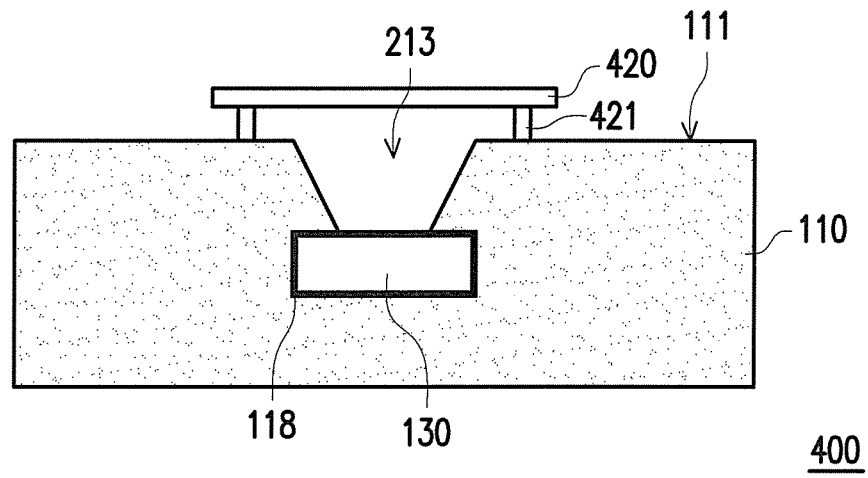
FIG. 4A and FIG. 4B are schematic views of the sample collection component according to another embodiment of the invention.
Figure 4B:
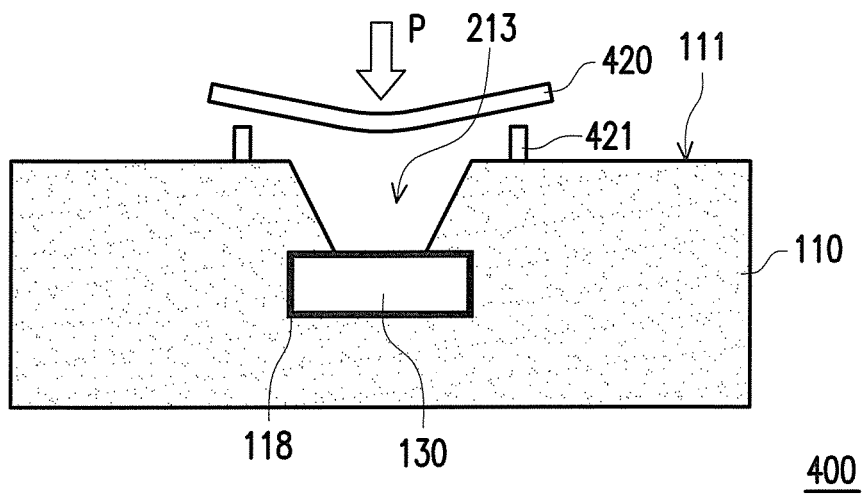

FIG. 4A and FIG. 4B are schematic views of the sample collection component according to another embodiment of the invention. Referring to FIG. 4A and FIG. 4B, a sample collection component 400 of this embodiment has a structure similar to the structure of the sample collection component 200 of FIG. 2. Therefore, identical or similar components are assigned with the same or similar reference numerals, and detailed description thereof is not repeated hereinafter. A difference between the sample collection component 400 of this embodiment and the sample collection component 300 of the previous embodiment is that: a removable light shielding component 420 of this embodiment is a light shielding structural member that is manufactured and completed at the same time as the main body 110, and the removable light shielding component 420 is connected with the main body 110 through a connection part 421. In other words, the sample collection component 400 already includes the removable light shielding component 420 when being completed. It is not required to additionally attach or deposit a light shielding structure onto the sample collection component 400. In this embodiment, the removable light shielding component 420 is a silicon structure, for example, or may be formed through a characteristic change of a construction material of the main body 110. For example, if the main body 110 includes a liquid crystal material, the liquid crystal material may change the light shielding effect by an electric field, so as to form the removable light shielding component 420 for shielding light. As shown in FIG. 4B, in this embodiment, after the loading of the liquid sample into the sample storing space 130 is completed, the removable light shielding component 420 is removed by an external force P, for example, so as to facilitate the subsequent sample observation performed by using a microscope device.

Figure 5A:
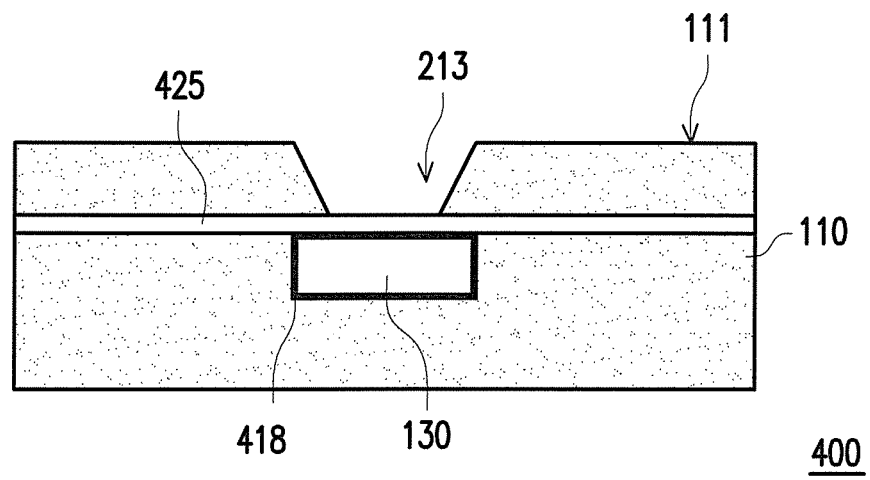
FIG. 5A and FIG. 5B are schematic views of the sample collection component according to another embodiment of the invention.
Figure 5B:
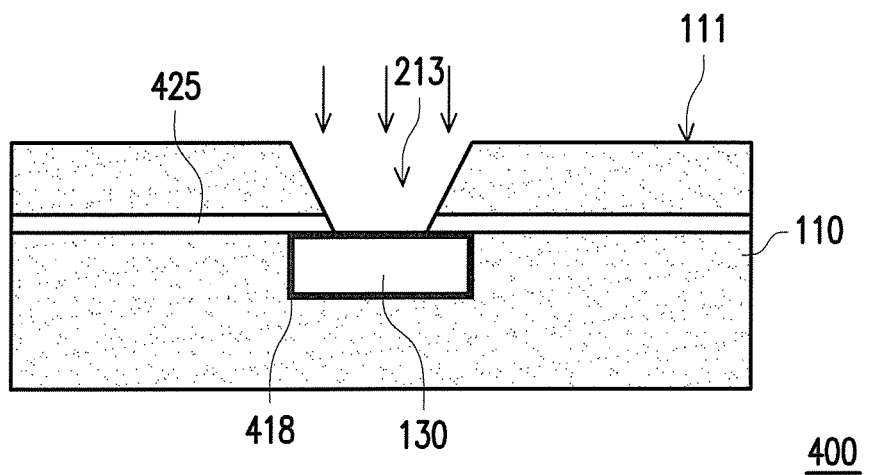

FIG. 5A and FIG. 5B are schematic views of the sample collection component according to another embodiment of the invention. Referring to FIG. 5A, in the sample collection component 400 of this embodiment, the removable light shielding component 425, formed of SiC for example, may be disposed corresponding to the sample storing space 130 directly by vapor deposition, sputtering, or spin coating simultaneously when the main body 110 is manufactured. In addition, the sample storing space 130 may be covered by a thin film 418 formed of silicon nitride, for example, which serves as an etch stop layer of the sample storing space 130 and forms the surface of contact between the sample storing space 130 and the liquid sample. Referring to FIG. 5B, after the loading of the liquid sample into the sample storing space 130 is completed, a portion of the removable light shielding component 425 that shields above the sample storing space 130 may be removed by plasma dry etching in the direction indicated by the arrow of FIG. 5B for performing the subsequent sample observation step.

Figure 6A:
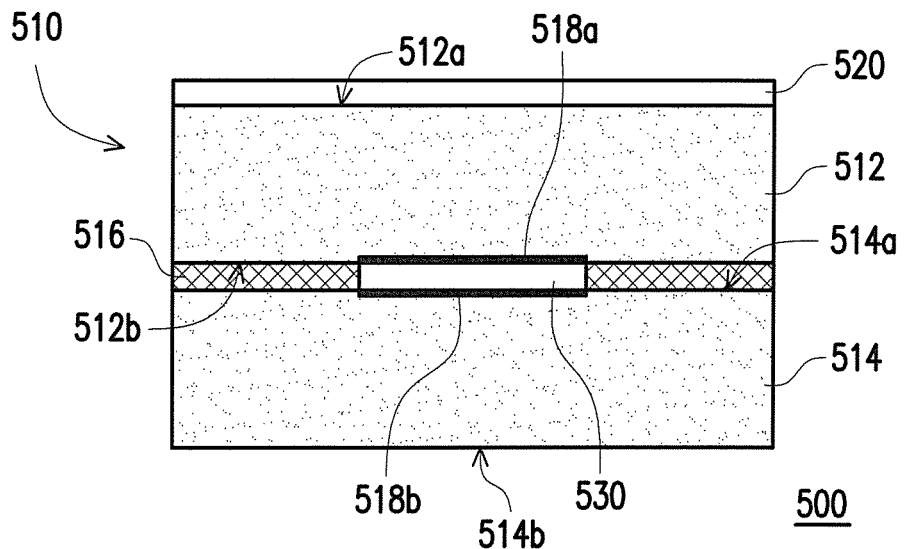
FIG. 6A is a schematic view of the sample collection component according to another embodiment of the invention.

FIG. 6A is a schematic view of the sample collection component according to another embodiment of the invention. Referring to FIG. 6A, a sample collection component 500 of this embodiment has a structure similar to the structure of the sample collection component 200 of the embodiment of FIG. 1A and FIG. 1B. Therefore, identical or similar components are assigned with the same or similar reference numerals, and detailed description thereof is not repeated hereinafter. In this embodiment, a difference between the sample collection component 500 and the sample collection component 200 is that: a main body 510 of the sample collection component 500 may include a first substrate 512, a second substrate 514, and a spacer 516. The first substrate 512 has a first surface 512a and a second surface 512b opposite to each other, and the second substrate 514 has a third surface 514a and a fourth surface 514b opposite to each other. Moreover, the first substrate 512 and the second substrate 514 are stacked on each other vertically, for example, and the second surface 512b of the first substrate 512 faces the third surface 514a of the second substrate 514.

In this embodiment, a material of the first substrate 512 and the second substrate 514 is a semiconductor material or a metal oxide material, for example. In addition, the semiconductor material is a double polished or single polished single crystal silicon, and the metal oxide is aluminum oxide, for example. The thicknesses of the first substrate 512 and the second substrate 514 may be changed according to the design or actual needs. For example, if the sample collection component 500 is applied for observation using an electron microscope, the thicknesses of the first substrate 512 and the second substrate 514 may be designed respectively to be in a range of about 0.2 mm to 0.8 mm.

As shown in FIG. 6A, the spacer 516 is disposed between the second surface 512b and the third surface 514a to connect and fix the first substrate 512 and the second substrate 514 and form a sample storing space 530 between the first substrate 512 and the second substrate 514. In this embodiment, the sample storing space 530 defined by the spacer 516 may be a flow channel that has openings at the front and rear ends. The liquid sample may enter the sample storing space 530 through the openings at the front and rear ends to be contained in the sample storing space 530.

In this embodiment, the spacer 516 may also maintain a distance between the first substrate 512 and the second substrate 514 and bond and fix the first substrate 512 and the second substrate 514. The spacer 516 has a height in a range of about 0.1 µm to 20 µm, or even in a range of 0.1 µm to 10 µm. In other words, the distance between the first substrate 512 and the second substrate 514, i.e., the height of the sample storing space 530, is in a range of 0.1 µm to 20 µm, or even in a range of 0.1 µm to 10 µm. The manufacturing and configuration method of this embodiment as described above has an advantage that: if the liquid sample contains suspended particles, some suspended particles that are greater than 10 µm in the liquid sample may be excluded from the sample storing space 530. Thus, the sample collection component 500 of this embodiment may be used for performing separation observation for blood cells and plasma in blood.

In this embodiment, considering the materials, manufacturing processes, and other possible factors of the first substrate 512 and the second substrate 514, the spacer 516 may be an adhesive material, such as epoxy resin, an ultraviolet glue, or a silicone material. Alternatively, the spacer 516 may be a non-adhesive material, such as silicon or an oxide thereof. Furthermore, the spacer 516 may be bonded between the first substrate 512 and the second substrate 514 by anodic bonding between silicon or a silicon oxide, for example. Moreover, the spacer 516 may be applied by screen printing and seal, for example, to be formed on the second surface 512b of the first substrate 512 and the third surface 514a of the second substrate 514. Alternatively, in the sample collection component 500, the spacer 516 may be formed on the second surface 512b of the first substrate 512 and the third surface 514a of the second substrate 514 by chemical vapor deposition.

In this embodiment, the main body 510 may have a first thin film 518a and a second thin film 518b, wherein the first thin film 518a is located on the second surface 512b of the first substrate 512 and the second thin film 518b is located on the third surface 514a of the second substrate 514. The first thin film 518a, the second thin film 518b, and the spacer 516 together maintain the sample storing space 530. In this embodiment, a method of forming the first thin film 518a and the second thin film 518b respectively on the second surface 512b and the third surface 514a includes chemical vapor deposition, acid washing, surface material deposition, and polymer deposition, wherein the chemical deposition method is performed by plasma enhanced chemical vapor deposition (PECVD), for example. Details regarding the method of forming the first thin film 518a and the second thin film 518b may be known from the current semiconductor manufacturing or MEMS (microelectromechanical) manufacturing technology and thus are not explained hereinafter.

A material of the first thin film 518a and the second material 518b may be selected from a group of silicon, silicon nitride, silicon oxide, silicon dioxide, silicon oxynitride, carbon, diamond film, silicon carbide, graphene, silicon carbide, aluminum oxide, titanium nitride, carbon oxide, and a combination thereof. In addition, the first thin film 518a and the second thin film 518b need to use a material that has a high electron penetration rate for an electron beam from a transmission electron microscope, for example, to pass through, so as to meet the observation requirement of the transmission electron microscope. Furthermore, the thicknesses of the first thin film 518a and the second thin film 518b may be changed according to the design or actual needs. For example, the first thin film 518a and the second thin film 518b respectively have a thickness that is in a range of about 2 nm to 200 nm, so as to facilitate the observation through a microscope device, such as transmission electron microscope. The above describes a silicon wafer manufacturing process as an example. Nevertheless, the invention may also be applied to other substrate materials considering the mechanical strength, density, light transmittance, electron penetration rate, process integration of the thin film and the substrate, residual stress, and surface properties of the thin film.

Furthermore, the first thin film 518a and the second thin film 518b of this embodiment may serve as the surface for contact with the liquid sample, which may be a hydrophilic material or a hydrophobic material. In this embodiment, the hydrophilic material may enhance the adsorption strength for adsorbing polar liquid sample. The hydrophobic material may enhance the adsorption strength for adsorbing nonpolar liquid sample. In addition, the surface properties of the first thin film 518a and the second thin film 518b may be physically modified through UV ozone modification or plasma modification, or be chemically modified by pickling, etching, anodizing, or connecting a functional group, for example.

In this embodiment, the removable light shielding component 520 covers the first surface 512a of the first substrate 512, and the removable light shielding component 520 may be a sheet material or a material layer formed by sputtering, vapor deposition, or spin coating. Moreover, a material for forming the removable light shielding component 520 may include a conductive material, such as gold, copper, and aluminum, or a semiconductor or non-conductive material, such as silicon, plastic, ceramics, or a polymer material.

Figure 6B:
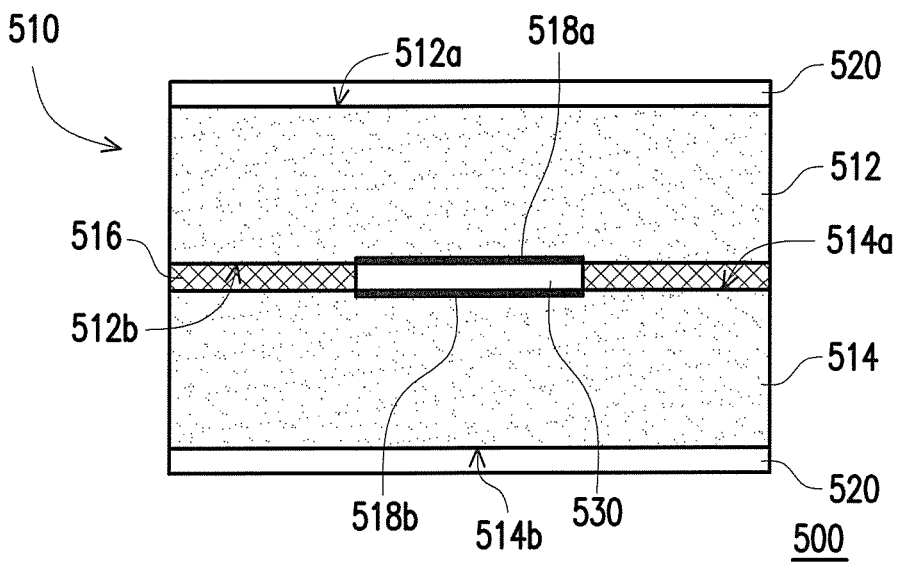
FIG. 6B is a schematic view of the sample collection component according to another embodiment of the invention.

FIG. 6B is a schematic view of the sample collection component according to another embodiment of the invention. Referring to FIG. 6A and FIG. 6B, in addition to using the removable light shielding component 520 to cover the first surface 512a of the first substrate 512 of the sample collection component 500 as shown in FIG. 6A, in this embodiment, the fourth surface 514b of the second substrate 514 of the sample collection component 500 may also be covered with the removable light shielding component 520 to enhance the light shielding effect of the sample collection component 500.

Figure 7A:
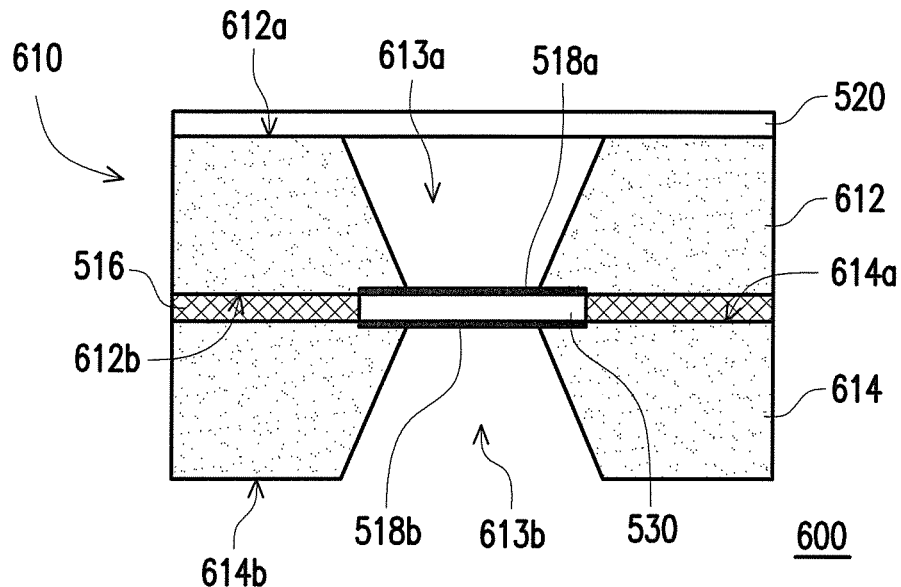
FIG. 7A, FIG. 7B, and FIG. 7C are schematic views of the sample collection component according to another embodiment of the invention.
Figure 7B:
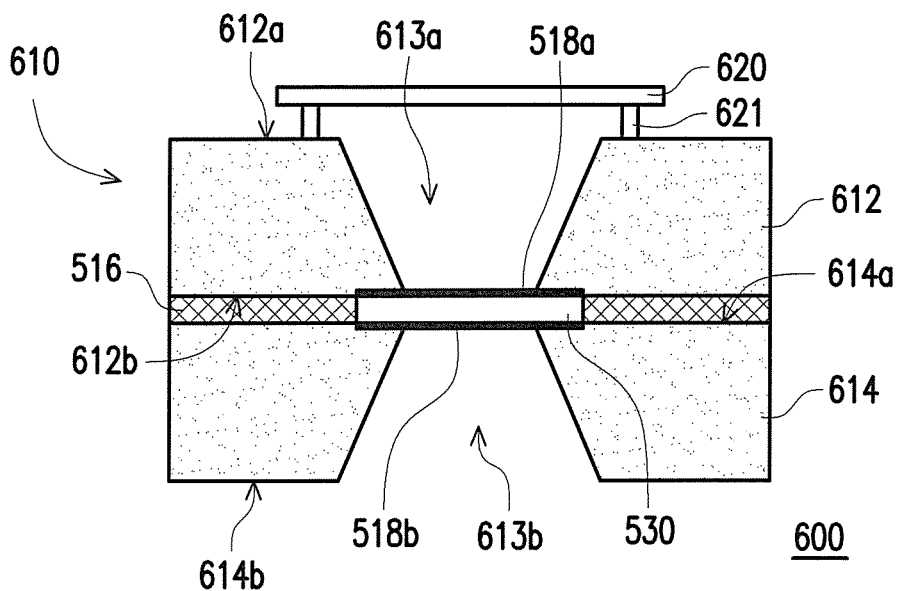
Figure 7C:
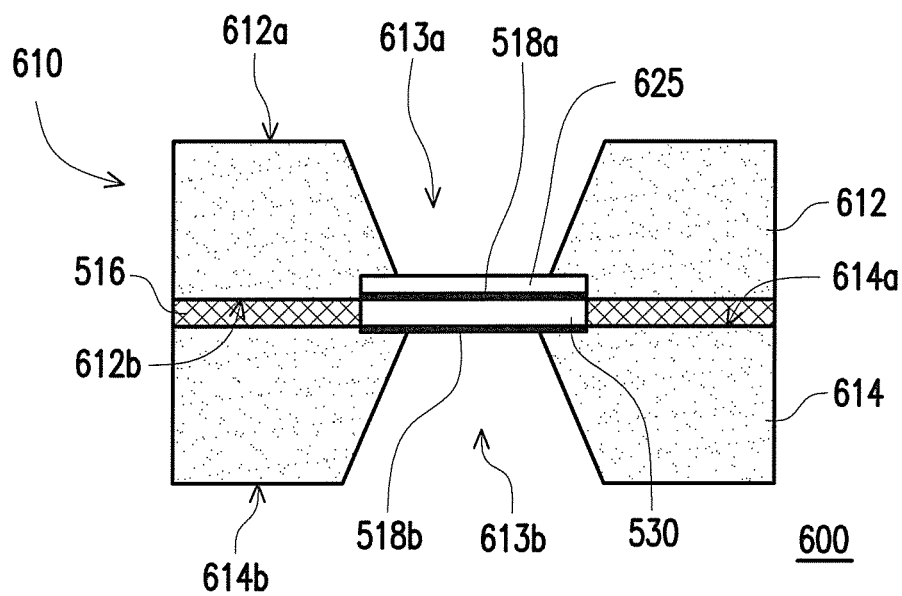

FIG. 7A, FIG. 7B, and FIG. 7C are schematic views of the sample collection component according to another embodiment of the invention. Referring to FIG. 7A, a sample collection component 600 of this embodiment has a structure similar to the structure of the sample collection component 500 of the embodiment of FIG. 6. Therefore, identical or similar components are assigned with the same or similar reference numerals, and detailed description thereof is not repeated hereinafter. A difference between the sample collection component 600 of this embodiment and the sample collection component 500 includes that: a first substrate 612 of a main body 610 of the sample collection component 600 includes a first recess on a second surface 612b to form a first observation window 613a that exposes the sample storing space 530, and a bottom of the first observation window 613a is connected with the first thin film 518a. Moreover, the removable light shielding component 520 may cover the first observation window 613a to form a sealed space in the first recess that forms the first observation window 613a.

Referring to FIG. 7B and FIG. 7C, in this embodiment, in addition to forming the removable light shielding component 520 with the sheet material or the material layer described above, removable light shielding components 620 and 625 may be manufactured simultaneously with the main body 610 of the sample collection component 600, as shown in FIG. 7B or FIG. 7C, to shield the light that enters the sample storing space 630 according to the actual needs. Referring to FIG. 7B, the removable light shielding component 620 has composition material and structure similar to those of the aforementioned removable light shielding component 420, and the removable light shielding component 620 may be manufactured simultaneously with the first substrate 612 of the main body 610 when the sample collection component 600 is manufactured, wherein the removable light shielding component 620 is connected with the first surface 612a of the first substrate 612 through a connection part 621. Moreover, after the loading of the liquid sample into the sample storing space 130 is completed, the removable light shielding component 620 may be removed by an external force, as shown in FIG. 4B.

Referring to FIG. 7C, in the sample collection component 600 of this embodiment, during the manufacturing process of the first substrate 612 of the main body 610, a removable light shielding component 625 that is formed of a SiC material for example may be applied to the second surface 612b of the first substrate corresponding to the sample storing space 530 to form the material layer for shielding the light. The removable light shielding component 625 of this embodiment has structure and composition material similar to those of the removable light shielding component 425. Moreover, after the loading of the liquid sample into the sample storing space 630 of the sample collection component 600 is completed, the removable light shielding component 625 may also be removed by plasma dry etching.

Referring to FIG. 7A, the second substrate 614 includes a second recess on the third surface 614a to form a second observation window 613b that exposes the sample storing space 530, and a bottom of the second recess is connected with the second thin film 518b. In this embodiment, the sample collection component 600 is placed on a working platform by the fourth surface 614b of the second substrate 614, for example. Therefore, a side of the fourth surface 614b of the second substrate 614 is shielded by the working platform directly and does not require a light shielding structure. In other embodiments not illustrated here, the sample collection component 600 may be placed on the working platform by the first surface 612a of the first substrate 612, and the removable light shielding component 520 may be disposed on the fourth surface 614b of the second substrate 614 instead.

Figure 8A:
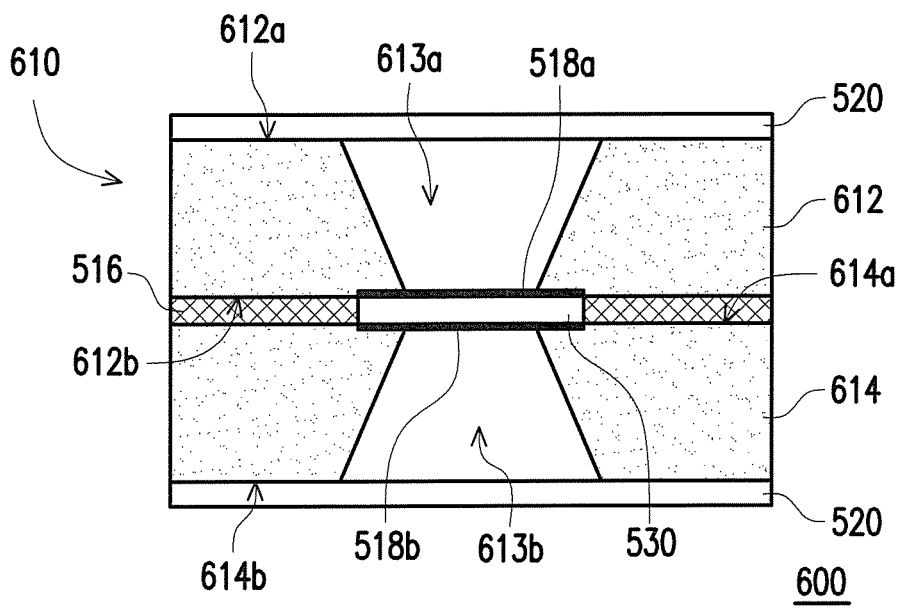
FIG. 8A, FIG. 8B, and FIG. 8C are schematic views of the sample collection component according to another embodiment of the invention.
Figure 8B:
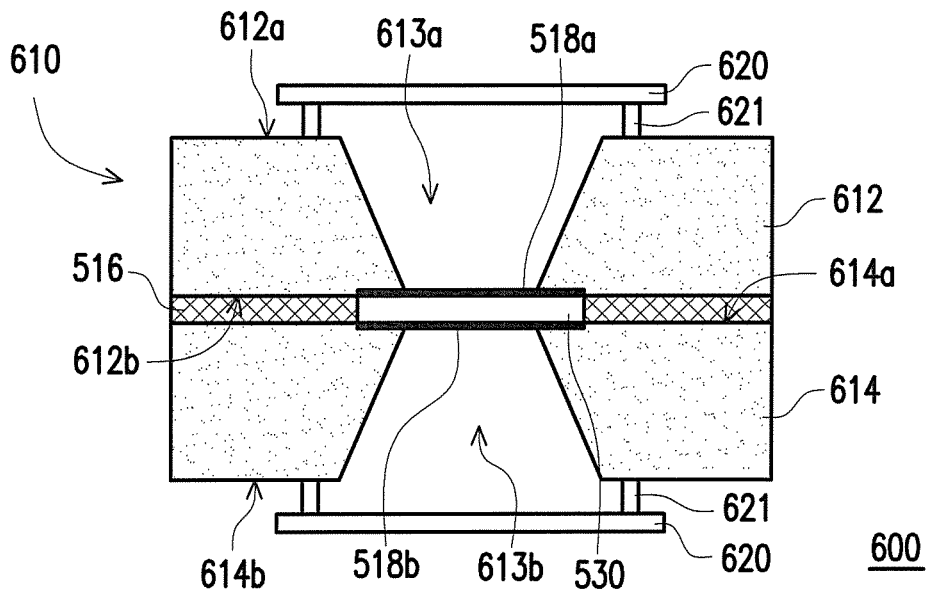
Figure 8C:
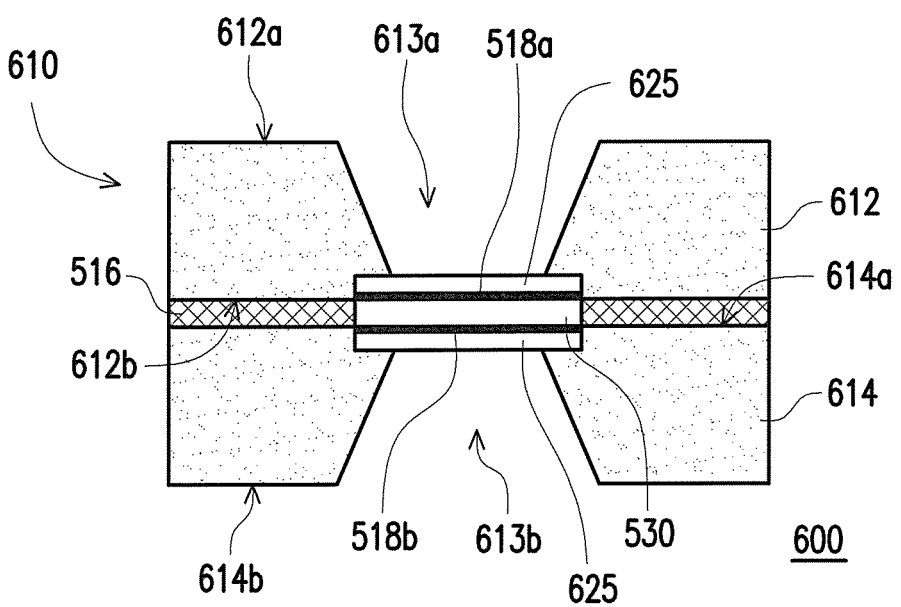

FIG. 8A, FIG. 8B, and FIG. 8C are schematic views of the sample collection component according to another embodiment of the invention. As shown in FIG. 8A, FIG. 8B, and FIG. 8C, in addition to the sample collection component 600 shown in FIG. 7A, FIG. 7B, and FIG. 7C, the removable light shielding component 520, 620, or 625 may be further disposed on the first surface 612a of the first substrate 612. In this embodiment, the removable light shielding component 520, 620, or 625 may also be disposed on the fourth surface 614b of the second substrate 614 of the sample collection component 600, so as to shield light for the first observation window 613a and the second observation window 613b of the sample collection component 600.

In particular, if the sample collection component 600 is not placed on the working platform, such as desktop, light may enter the sample storing space 530 through the second observation window 613b formed in the second substrate 614. Therefore, by disposing the removable light shielding component 520, 620, or 625 on both the first surface 612a of the first substrate 612 and the fourth surface 614b of the second substrate 614, light leakage is prevented and the light shielding effect for the sample storing space 530 is enhanced.

Figure 9:
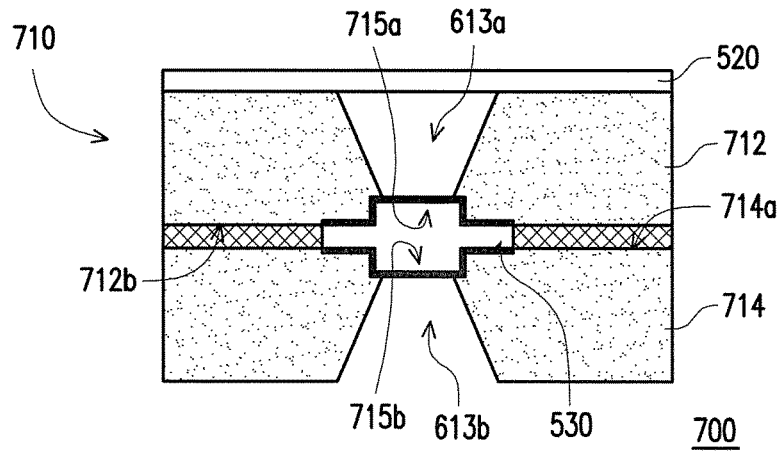
FIG. 9 is a schematic view of the sample collection component according to another embodiment of the invention.

FIG. 9 is a schematic view of the sample collection component according to another embodiment of the invention. A sample collection component 700 of this embodiment has a structure similar to the structure of the sample collection component 600 of FIG. 7A, FIG. 7B, and FIG. 7C. Therefore, identical or similar components are assigned with the same or similar reference numerals, and detailed description thereof is not repeated hereinafter. In this embodiment, grooves 715a and 715b may be formed respectively on the second surface 712b of the first substrate 712 and the third surface 714a of the second substrate 714 of the sample collection component 700 corresponding to the sample storing space 530. In the sample collection component 700, the amount of the liquid sample that can be stored in the sample storing space 530 is adjustable by changing the sizes of the grooves 715a and 715b.

Moreover, the sample collection component 700 may be similar to the sample collection component 500 and further have the removable light shielding component 520 on the main body 710. Alternatively, the sample collection component 700 may be similar to the sample collection component 600, in which the removable light shielding component 620 or 625 is formed simultaneously when the main body 710 is manufactured.

Figure 10A:
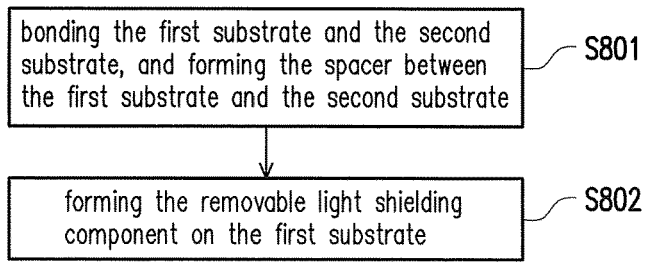
FIG. 10A is a flowchart showing the manufacturing method of the sample collection component according to an embodiment of the invention.

FIG. 10A is a flowchart showing the manufacturing method of the sample collection component according to an embodiment of the invention. Referring to FIG. 7A and FIG. 10A, in this embodiment, the manufacturing method of the sample collection component 500 includes: bonding the first substrate 612 to the second substrate 614, and forming the spacer 516 between the first substrate 612 and the second substrate 614 (Step S801) to connect and fix the first substrate 612 and the second substrate 614, so as to form the sample storing space 530, which is sealable and allows light to pass through, between the first substrate 612 and the second substrate 614. Then, the removable light shielding component 520 is formed on the first substrate 512 (Step S802). The removable light shielding component 520 corresponds to the sample storing space 530 and shields at least a portion of the light that passes through the sample storing space 530.

In this embodiment, the removable light shielding component 520 is a sheet material, for example, which is attached onto the first substrate 612 by external overlap, clamping, or electrostatic adsorption. Alternatively, the removable light shielding component 520 may be a material layer formed on the first substrate 612 by vapor deposition, sputtering, or coating. The sample collection component 500 shields at least a portion of the light that enters the sample storing space 530 with the removable light shielding component 520.

Referring to FIG. 7A again, in this embodiment, like the aforementioned sample collection component 600, the sample collection component 500 may further have the first recess formed on the first surface 612a of the first substrate 612 corresponding to the sample storing space 530, so as to form the first observation window 613a that exposes the sample storing space 530. In addition, the first observation window 613a may be temporarily covered by the removable light shielding component 520, which is formed of a sheet material for example, so as to form a sealed space of a particular pressure in the first observation window 613a. The pressure is in a range of 0.01 KPa to 150 KPa, for example, to enhance the stability of the sheet material attached onto the first surface 612a.

Figure 10B:
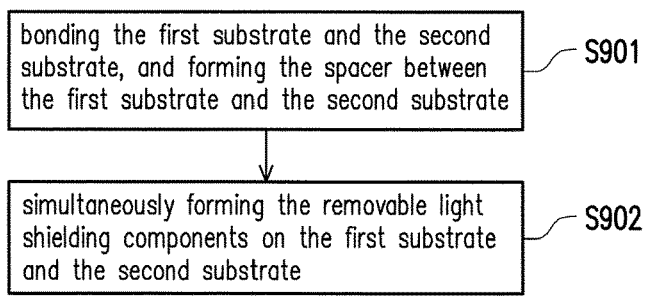
FIG. 10B is a flowchart showing the manufacturing method of the sample collection component according to another embodiment of the invention.

FIG. 10B is a flowchart showing the manufacturing method of the sample collection component according to an embodiment of the invention. Referring to FIG. 8A and FIG. 10B, in the manufacturing process of the sample collection component 600, after the bonding of the first substrate 612 to the second substrate 614 is completed and the spacer 516 is formed between the first substrate 612 and the second substrate 614 (Step S901), in addition to forming the removable light shielding component 520 on the first substrate 612 of the sample collection component 600 as shown in FIG. 10A, in this embodiment, the removable light shielding component 520 may be simultaneously formed on the second substrate 614 of the sample collection component 600 (Step S902), so as to provide the light shielding effect for both the first observation window 613a and the second observation window 613b of the sample collection component 600 and enhance the light shielding effect of the sample storing space 530.

Figure 11A:
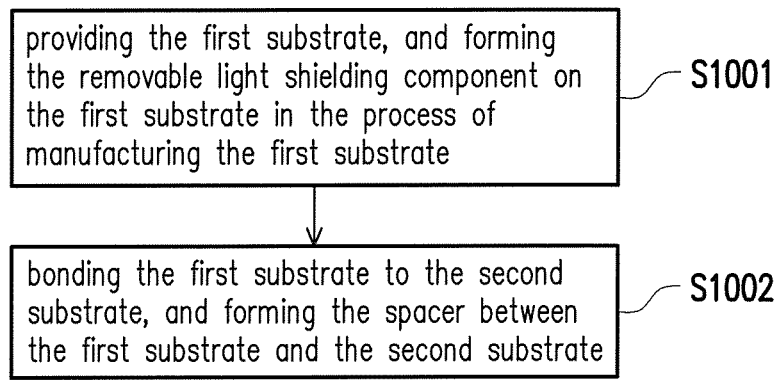
FIG. 11A is a flowchart showing the manufacturing method of the sample collection component according to another embodiment of the invention.

FIG. 11A is a flowchart showing the manufacturing method of the sample collection component according to another embodiment of the invention. Referring to FIG. 7C and FIG. 11A, in this embodiment, the manufacturing method of the sample collection component 600 includes providing the first substrate 612, and the removable light shielding component 625 is formed on the first substrate 612 in the process of manufacturing the first substrate 612 (Step S1001). Then, the first substrate 612 is bonded to the second substrate 614 and the spacer 516 is formed between the first substrate 612 and the second substrate 614 (Step S1002) to form the sample storing space 530 that is sealable and allows light to pass through between the first substrate 612 and the second substrate 614. In this embodiment, the removable light shielding component 625 is disposed corresponding to the sample storing space 530 to shield at least a portion of the light that passes through the sample storing space 530.

As described above, the first surface 612a of the first substrate 612 in this embodiment may be formed with the first recess corresponding to the sample storing space 530, so as to form the first observation window 613a that exposes the sample storing space 530. Moreover, the removable light shielding component 625 of this embodiment may be a material layer formed of SiC, which is disposed on the bottom surface of the first observation window 613a and extends to a portion of a junction between the sample storing space 530 and the first substrate 612.

In this embodiment, in the manufacturing method of the sample collection component 600, the removable light shielding component 620 may be used as the light shielding structure, as shown in FIG. 7B. As described above, the removable light shielding component 620 is a structural member formed simultaneously with the first substrate 612, and the removable light shielding component 620 may be connected with the first substrate 612 through the connection part 621 to shield at least a portion of the light that passes through the sample storing space 530.

Figure 11B:
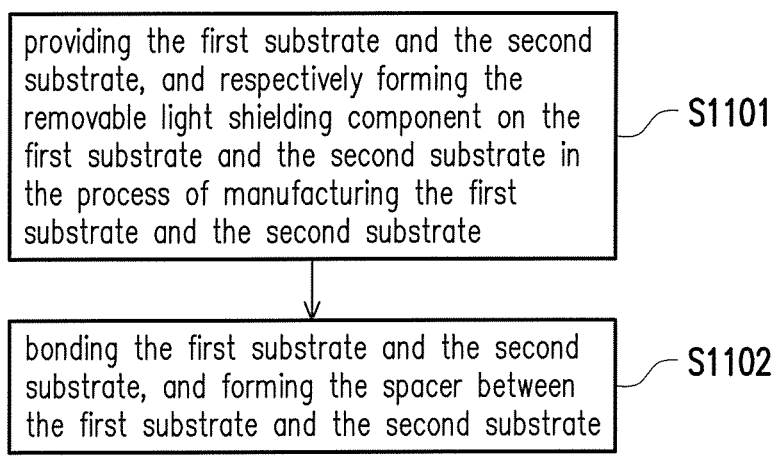
FIG. 11B is a flowchart showing the manufacturing method of the sample collection component according to another embodiment of the invention.

FIG. 11B is a flowchart showing the manufacturing method of the sample collection component according to an embodiment of the invention. Referring to FIG. 8C and FIG. 11B, in the manufacturing method of the sample collection component 600 in this embodiment, in addition to forming the removable light shielding component 625 on the first substrate 612 in the step of manufacturing the first substrate 612 as shown in FIG. 11A, the removable light shielding component 520 may be formed on the second substrate 614 while the second substrate 614 is manufactured (Step S1101). Then, the first substrate 612 and the second substrate 614 respectively having the removable light shielding component 520 formed on the surfaces thereof are bonded to each other, and the spacer 516 is formed between the first substrate 612 and the second substrate 614 (Step S1102).

To sum up, the sample collection component disclosed in the above embodiments of the invention is provided with the removable light shielding component to shield at least a portion of the light that passes through the sample storing space. Before the liquid sample is loaded into the sample storing space, the removable light shielding component prevents unnecessary light from entering the sample storing space through the main body of the sample collection component by filtering, reflecting, or absorbing the light. Therefore, before observation is performed with a microscope device, such as an electron microscope, the removable light shielding component prevents the fluidity or component properties of the liquid sample from being changed due to irradiation of external light or reaction between the components of the liquid sample and the light, which may affect the observation result.

It will be apparent to those skilled in the art that various modifications and variations can be made to the disclosed embodiments without departing from the scope or spirit of the invention. In view of the foregoing, it is intended that the invention covers modifications and variations provided that they fall within the scope of the following claims and their equivalents.

What is claimed is:

1. A sample collection component, comprising:
   a main body having a sample storing space which is sealable and allows a light to pass through; and
   a removable light shielding component disposed on the main body and located outside the sample storing space for shielding at least a portion of the light that passes through the sample storing space,
   wherein the main body comprises:
   a first substrate having a first surface and a second surface opposite to each other;
   a second substrate having a third surface and a fourth surface opposite to each other, wherein the first substrate and the second substrate are stacked on each other and the second surface faces the third surface;
   a spacer disposed directly between the second surface and the third surface and connecting and fixing the first substrate and the second substrate to form the sample storing space between the first substrate and the second substrate;
   a first film located on the second surface of the first substrate;
   a second film located on the third surface of the second substrate, wherein the first film, the second film, and the spacer together surround the sample storing space;
   a first groove formed on the second surface of the first substrate, where at least a portion of the first film is deposited on an internal surface of the first groove; and
   a second groove formed on the third surface of the second substrate, where at least a corresponding portion of the second film is deposited on a corresponding internal surface of the second groove,
   wherein a thickness of the first groove is smaller than a thickness of the first substrate, and a thickness of the second groove is smaller than a thickness of the second substrate.

2. The sample collection component according to claim 1, wherein the removable light shielding component comprises a sheet material that is attached onto the main body and covers at least a portion of the sample storing space.

3. The sample collection component according to claim 2, wherein the main body comprises a recess corresponding to the sample storing space for forming an observation window that exposes the sample storing space, and the sheet material seals the recess to form a sealed space of a particular pressure in the recess.

4. The sample collection component according to claim 1, wherein the removable light shielding component comprises a material layer that covers a surface of the main body and at least a portion of the sample storing space.

5. The sample collection component according to claim 1, wherein the first substrate comprises a first recess located on the first surface and a bottom of the first recess is connected with the first film to form a first observation window that exposes the sample storing space, and the removable light shielding component is disposed on the first observation window to shield at least a portion of the light that passes through the sample storing space.

6. The sample collection component according to claim 5, wherein the second substrate comprises a second recess located on the fourth surface and a bottom of the second recess is connected with the second film to form a second observation window that exposes the sample storing space.

7. The sample collection component according to claim 1, wherein the removable light shielding component comprises a light filtering material or a light valve component.

8. The sample collection component according to claim 7, wherein the light filtering material shields a light having a wavelength of 100 nm to 1 mm.

9. The sample collection component according to claim 1, wherein a material of the removable light shielding component comprises a conductor of gold, copper, or aluminum, or a semiconductor of silicon, or a non-conductor of plastic, ceramics, or a polymer material.

* * * * *